US011369647B2

(12) United States Patent
Kim et al.

(10) Patent No.: US 11,369,647 B2
(45) Date of Patent: Jun. 28, 2022

(54) PROBIOTICS FOR INHIBITING AND PREVENTING PROGRESSION OF RENAL DISEASES, AND COMPOSITIONS FOR INHIBITING AND PREVENTING PROGRESSION OF RENAL DISEASES COMPRISING SAME

(71) Applicant: Green Cross Wellbeing Corporation, Seongnam-si (KR)

(72) Inventors: Su Ae Kim, Seongnam-si (KR); Chang Taek Oh, Seongnam-si (KR); Jong Hun Lee, Seongnam-si (KR); Su Hwan Lim, Seongnam-si (KR); Jeom Yong Kim, Seongnam-si (KR); Sun Kyu Park, Seongnam-si (KR); Min Jung Jang, Seongnam-si (KR); Min Ju Lim, Seongnam-si (KR)

(73) Assignee: Green Cross Wellbeing Corporation, Seoul (KR)

( * ) Notice: Subject to any disclaimer, the term of this patent is extended or adjusted under 35 U.S.C. 154(b) by 0 days.

(21) Appl. No.: 16/772,869

(22) PCT Filed: Dec. 13, 2018

(86) PCT No.: PCT/KR2018/015883
§ 371 (c)(1),
(2) Date: Jun. 15, 2020

(87) PCT Pub. No.: WO2019/117654
PCT Pub. Date: Jun. 20, 2019

(65) Prior Publication Data
US 2021/0169951 A1 Jun. 10, 2021

(30) Foreign Application Priority Data
Dec. 15, 2017 (KR) .................. 10-2017-0173590

(51) Int. Cl.
*A61K 35/74* (2015.01)
*A61K 35/747* (2015.01)
*A23L 33/135* (2016.01)

(52) U.S. Cl.
CPC .......... *A61K 35/747* (2013.01); *A23L 33/135* (2016.08)

(58) Field of Classification Search
None
See application file for complete search history.

(56) References Cited

U.S. PATENT DOCUMENTS

| | | |
|---|---|---|
| 2002/0187134 A1 | 12/2002 | Ranaganthan et al. |
| 2006/0270020 A1 | 11/2006 | Boileau et al. |
| 2010/0316618 A1 | 12/2010 | Tsuboi et al. |
| 2011/0002902 A1 | 1/2011 | Asada et al. |
| 2011/0097307 A1 | 4/2011 | Ranganathan |
| 2011/0178103 A1 | 7/2011 | Matsuda et al. |
| 2014/0161780 A1 | 6/2014 | Ranganathan |
| 2017/0224717 A1 | 8/2017 | Nakashima et al. |
| 2017/0326186 A1 | 11/2017 | Mogna |
| 2018/0271919 A1 | 9/2018 | Van Hemert |
| 2019/0240270 A1 | 8/2019 | Kim et al. |

FOREIGN PATENT DOCUMENTS

| | | |
|---|---|---|
| EP | 3 459 369 A1 | 3/2019 |
| JP | 2008-545428 A | 12/2008 |
| JP | 4693085 B2 | 6/2011 |
| JP | 2013-209396 A | 10/2013 |
| KR | 10-2010-0109911 A | 10/2010 |
| KR | 10-2010-0126521 A | 12/2010 |
| KR | 10-2012-0039381 A | 4/2012 |
| KR | 10-2013-002545 A | 1/2013 |
| KR | 10-2014-0026326 A | 3/2014 |
| KR | 10-1587071 B1 | 1/2016 |
| KR | 10-1684289 B1 | 12/2016 |
| KR | 10-2017-0053723 A | 5/2017 |
| KR | 10-2017-0084127 A | 7/2017 |
| KR | 10-2017-0129718 A | 11/2017 |
| KR | 10-2018-0004840 A | 1/2018 |
| KR | 10-2018-0125895 A | 11/2018 |
| KR | 10-2019-0073363 A | 6/2019 |
| WO | 2005032591 A1 | 4/2005 |
| WO | 2014/148881 A1 | 9/2014 |

OTHER PUBLICATIONS

Bentley, R. (Jul. 11, 2017. Blog, Probiotic Education, Product Information; https://humarian.com/I-salivarius/).*
Fagundes et al (Braz. J. Nephrol. Jul.-Sep. 2018. 40(3):278-286).*
Guida et al., "Effect of short-term synbiotic treatment on plasma p-cresol levels in patients with chronic renal failure: A randomized clinical trial", Nutrition, Metabolism & Cardiovascular Diseases, vol. 24, 2014, pp. 1043-1049.
Khalil et al., "Evaluation of the probiotic potential of lactic acid bacteria isolated from faeces of breast-fed infants in Egypt", African Journal of Biotechnology, vol. 6, No. 7, Apr. 2, 2007, pp. 939-949.
Koppe et al., "Probiotics and chronic kidney disease", 2015 International Society of Nephrology, Jun. 10, 2015, pp. 1-9.
Twombley et al., "New Paradigms for the Use of Prebiotics, Probiotics, and Synbiotics in Renal Disease", Dialysis & Transplantation, May 2011, pp. 200-204.
Tan et al., "Indoxyl sulfate, a valuable biomarker in chronic kidney disease and dialysis" Hemodialysis International, vol. 21, 2017, pp. 161-167.

(Continued)

*Primary Examiner* — Jennifer E Graser
(74) *Attorney, Agent, or Firm* — Sughrue Mion, PLLC

(57) ABSTRACT

A probiotic for inhibiting and preventing the progression of a renal disease and a composition containing the same are disclosed. The probiotic contains a novel *Lactobacillus acidophilus* BP105 strain, a novel *Lactobacillus salivarius* BP121 strain. The novel probiotics, the *Lactobacillus acidophilus* BP105 strain and the *Lactobacillus salivarius* BP121 strain exhibit excellent indoxyl sulfate removal ability, p-cresol removal ability, and phosphorus absorption ability.

6 Claims, 9 Drawing Sheets

Specification includes a Sequence Listing.

(56) References Cited

OTHER PUBLICATIONS

Brocca et al., "Cytotoxic Effects of p-Cresol in Renal Epithelial Tubular Cells", Blood Purification, vol. 36, 2013, pp. 219-225.
Hruska et al., "The Roles of the Skeleton and Phosphorus in the CKD Mineral Bone Disorder", Adv Chronic Kidney Dis, Mar. 2011, vol. 18, No. 2, pp. 98-104.
Park, et al., "Atypical Progression of Acute Renal Failure Associated with Cisplatin Chemotherapy" The Korean Journal of Medicine, vol. 85, No. 4, 2013, pp. 425-429.
Kim, et al., "Investigation of the Expression of Fractalkine and the Infiltration Characteristics of Fractalkine Receptor Positive Cells and Macrophages in Cisplatin-induced Acute Renal Failure in Mice", The Korean Journal of Nephrology, 2008, Vo. 27, pp. 642-649.
Nataatmadja et al., "The Roles of Indoxyl Sulphate and p-Cresyl Sulphate in Patients with Chronic Kidney Disease: A Review of Therapeutic Options", Intech, Chapters, 2018, p. 181-197 (19 pages total).
Schulman et al., "AST-120 for the management of progression of chronic kidney disease", International Journal of Nephrology and Renovascular Disease, vol. 7, 2014, pp. 49-56.
Yamaguchi, et al., "Effect of AST-120 in Chronic Kidney Disease Treatment: Still a Controversy?", Nephron Clinical Practice, vol. 135, 2017, pp. 201-206.
Barcza Stockler-Pinto et al., "Indoxyl Sulfate and p-Cresyl Sulfate in Chronic Kidney Disease. Could These Toxins Modulate the Antioxidant Nrf2-Keap1 Pathway?", Journal of Renal Nutrition, vol. 24, No. 5 Sep. 2014, pp. 286-291.
Yoshifuji et al., "Gut Lactobacillus protects against the progression of renal damage by modulating the gut environment in rats", Nephrol Dial Transplant, vol. 31, 2016, pp. 401-412.
URL: http://www.ezbiocloud.net, Database updated May 13, 2020, Retrieved Jul. 10, 2020, 5 pages.
Alessandro Di Cerbo et al., "Clinical and experimental use of probiotic formulations for management of end-stage renal disease: an update", Int Urol Nephrol, 2013, vol. 45, XP035374261, pp. 1569-1576 (8 pages).
KCCM12169P; Budapest Treaty On The International Recognition Of The Deposit Of Microorganisms For The Purposes Of Patent Procedure, Nov. 16, 2017, 2 pages.
KCCM12170P; Budapest Treaty On The International Recognition Of The Deposit Of Microorganisms For The Purposes Of Patent Procedure, Nov. 16, 2017, 2 pages.
Fujii et al., "Role of oxidative stress and indoxyl sulfate in progression of cardiovascular disease in chronic kidney disease", Therapeutic Apheresis and Dialysis, vol. 15, No. 2, 2011, pp. 125-128.
Lim et al., "The effect of lactic acid bacteria isolates on the urinary tract pathogens to infants in vitro", Journal of Korean Medical Science, vol. 24, 2009, pp. 57-62.
Guida et al., "Effect of short-term synbiotic treatment on plasma p. cresol levels in patients with chronic Yenal failure: A randomized clinical trial", Nutrition, Metabolism & Cardiovascular Diseases, vol. 24, 2014, pp. 1043-1049.

\* cited by examiner

[Figure 1]
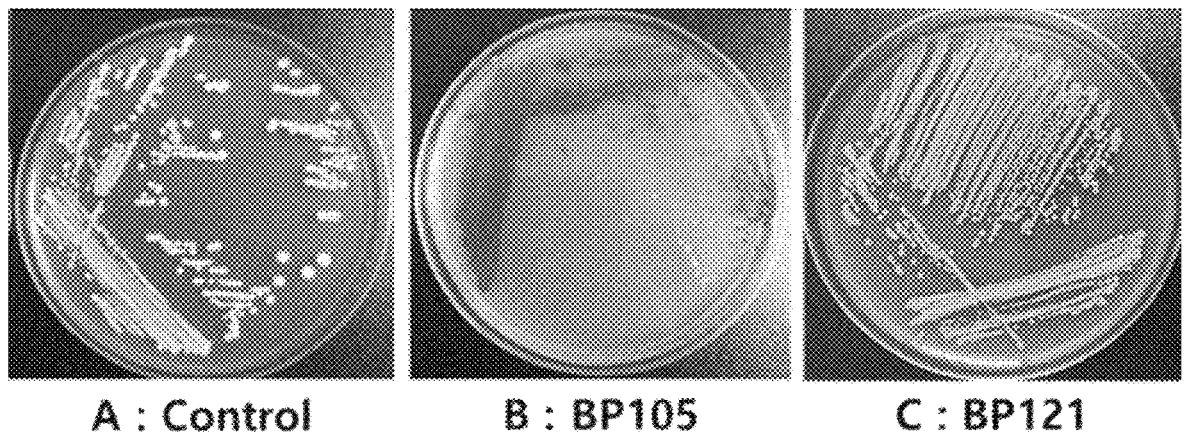

[Figure 2]
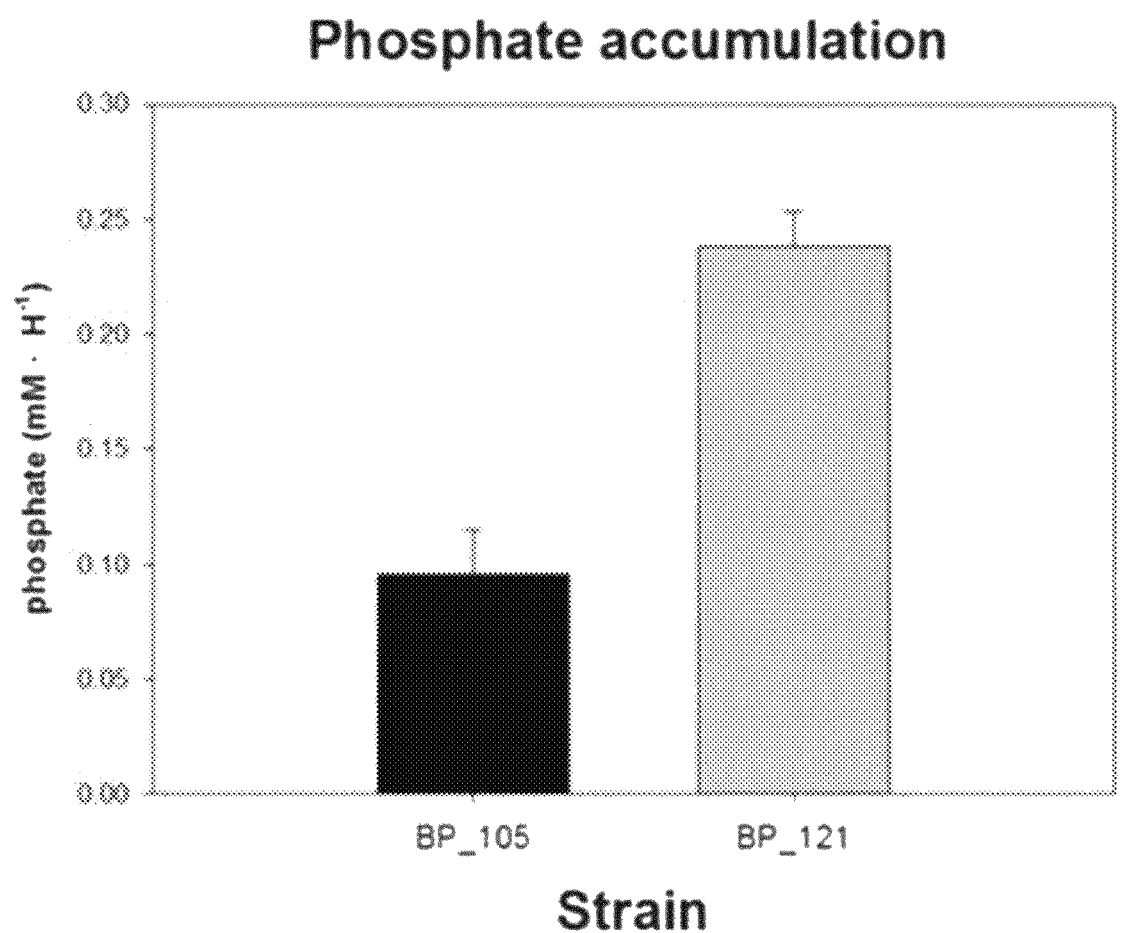

【Figure 3】
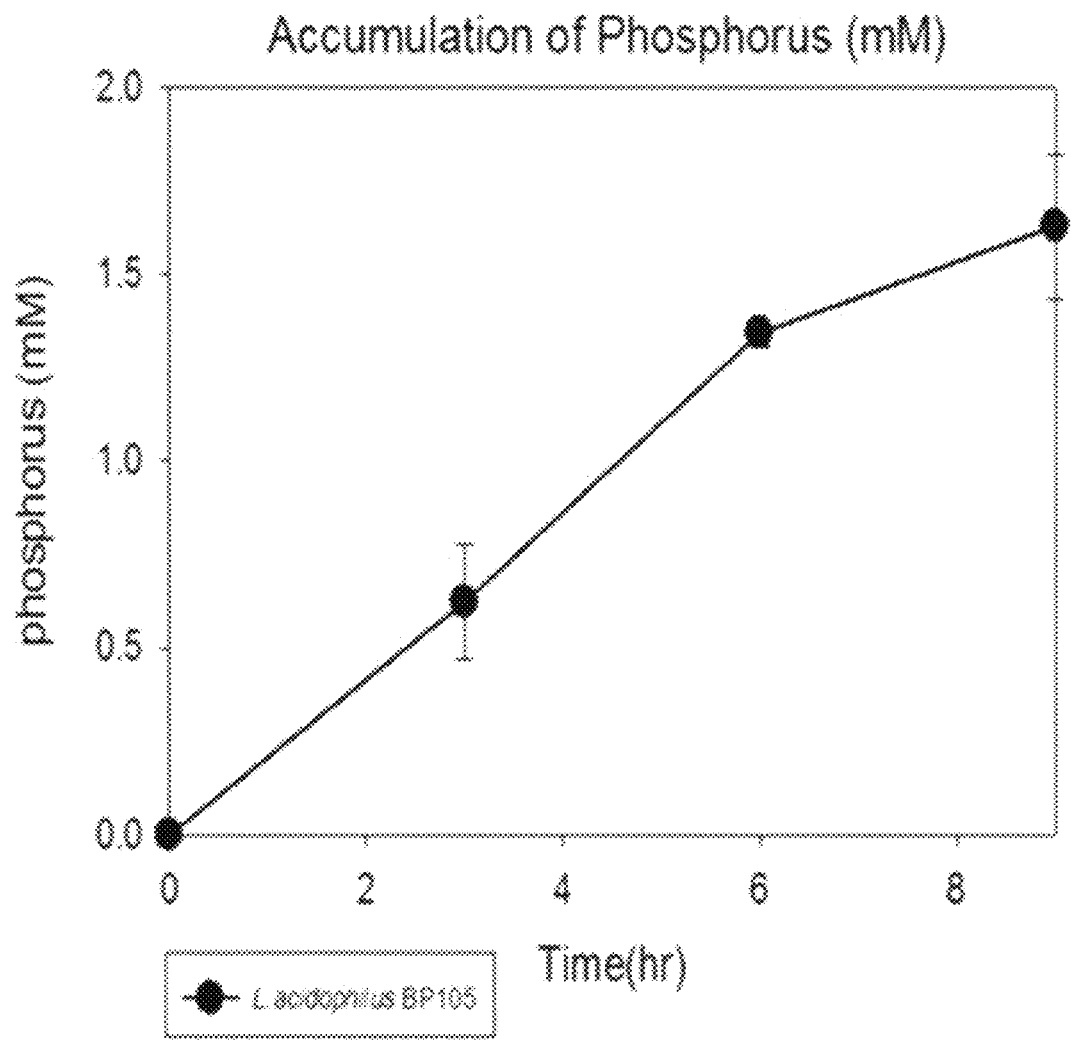

【Figure 4】
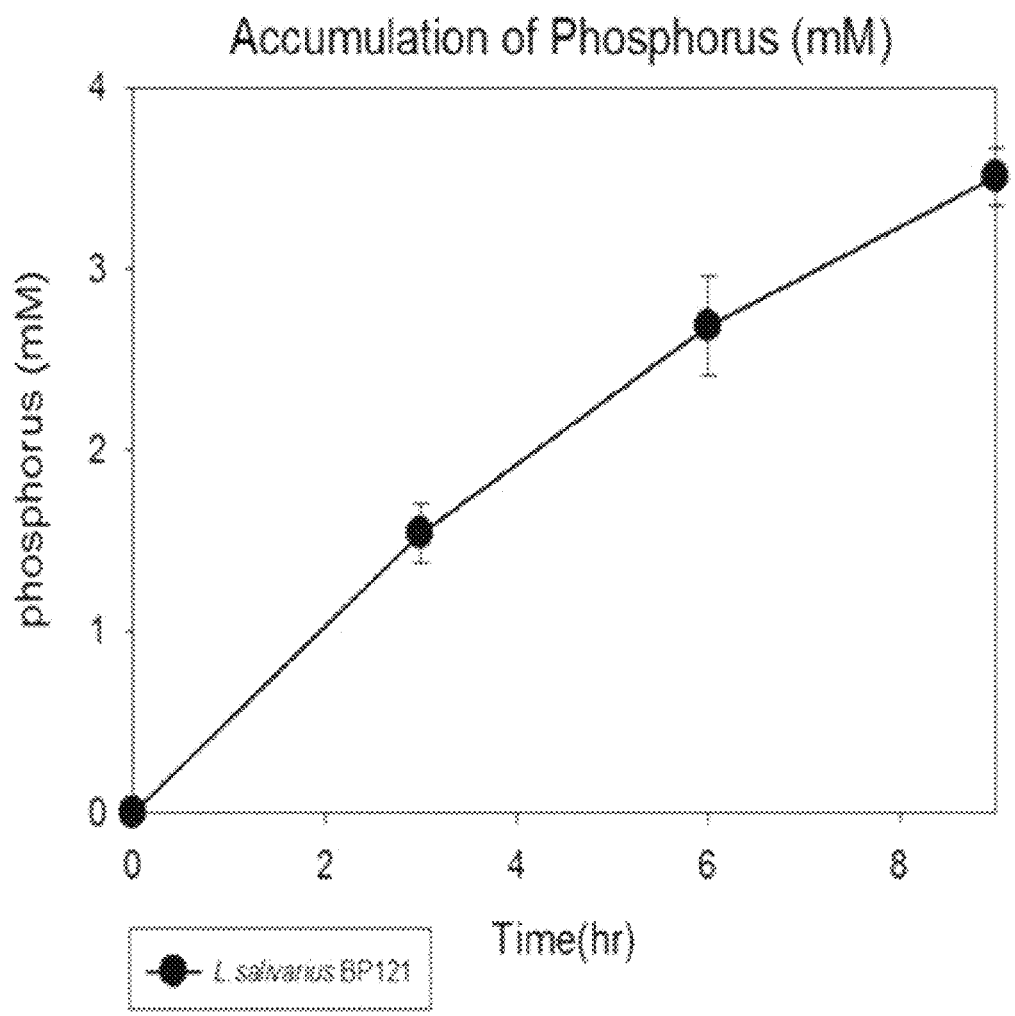

[Figure 5]
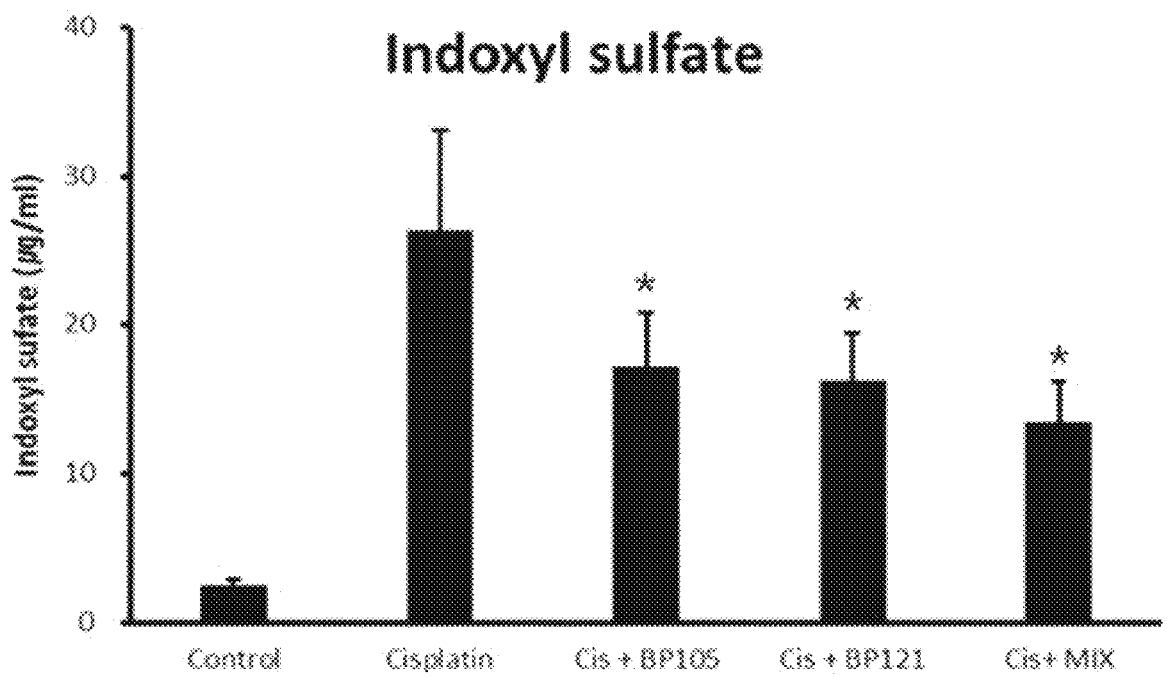

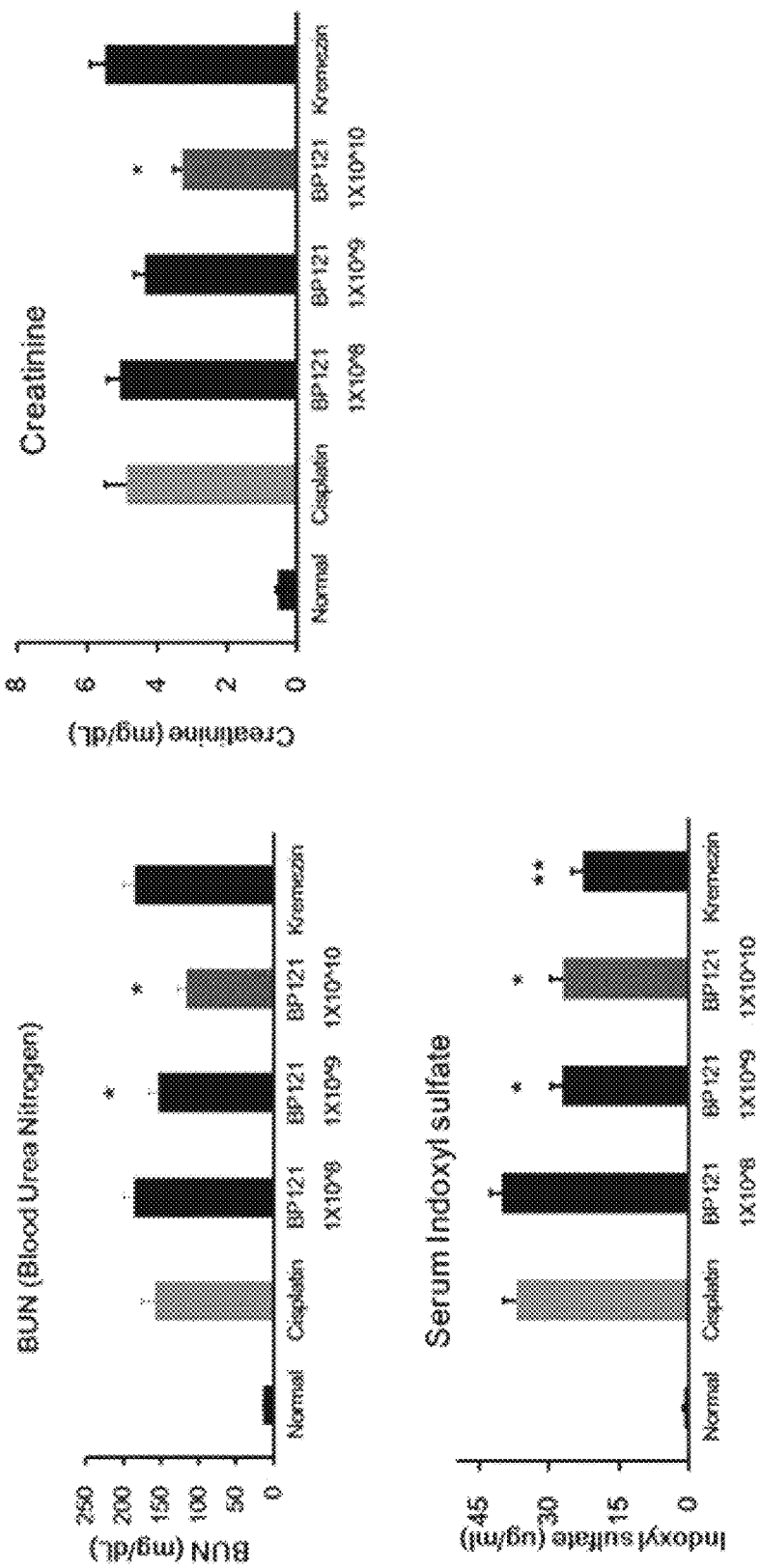
[Figure 6]

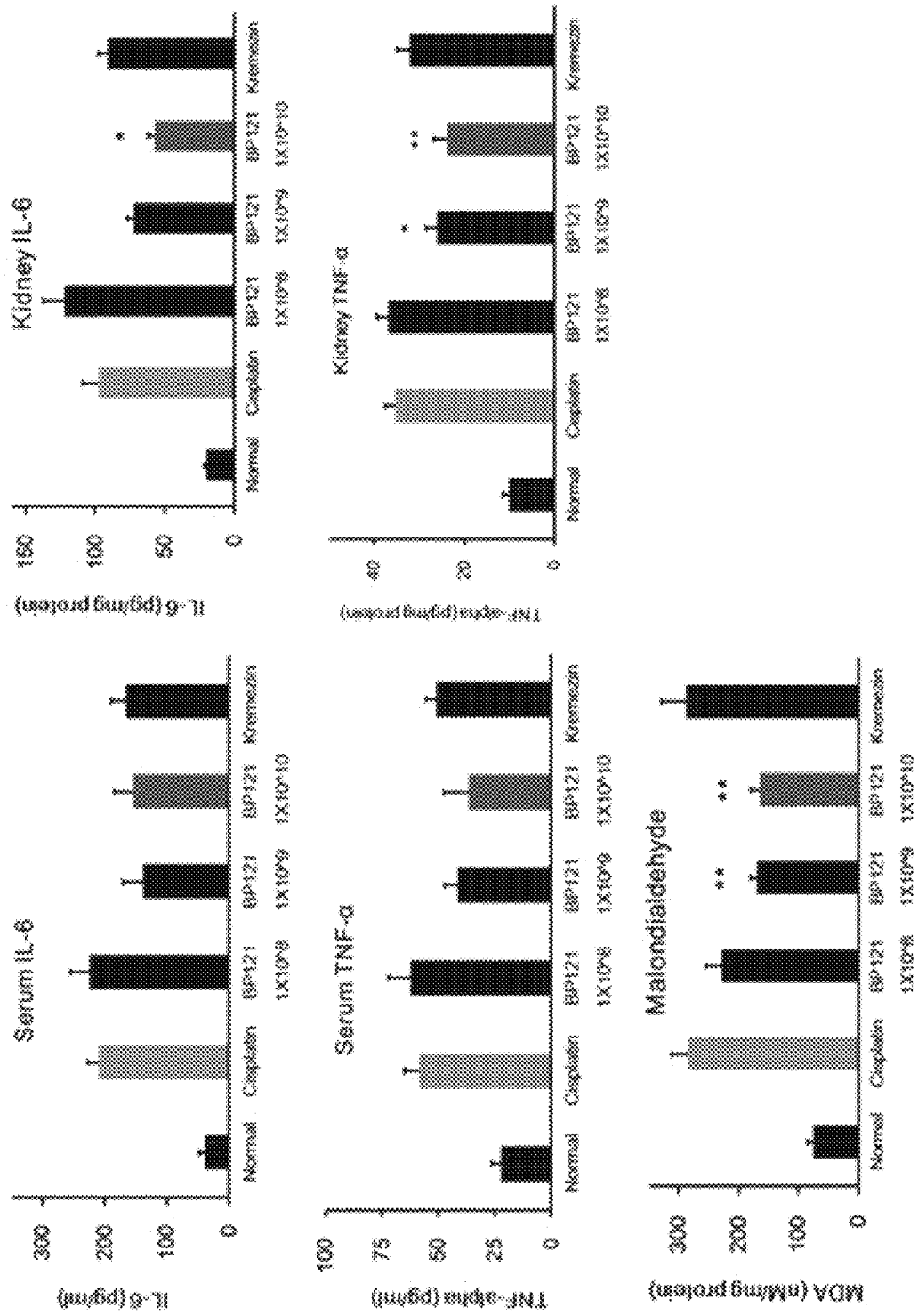
[Figure 7]

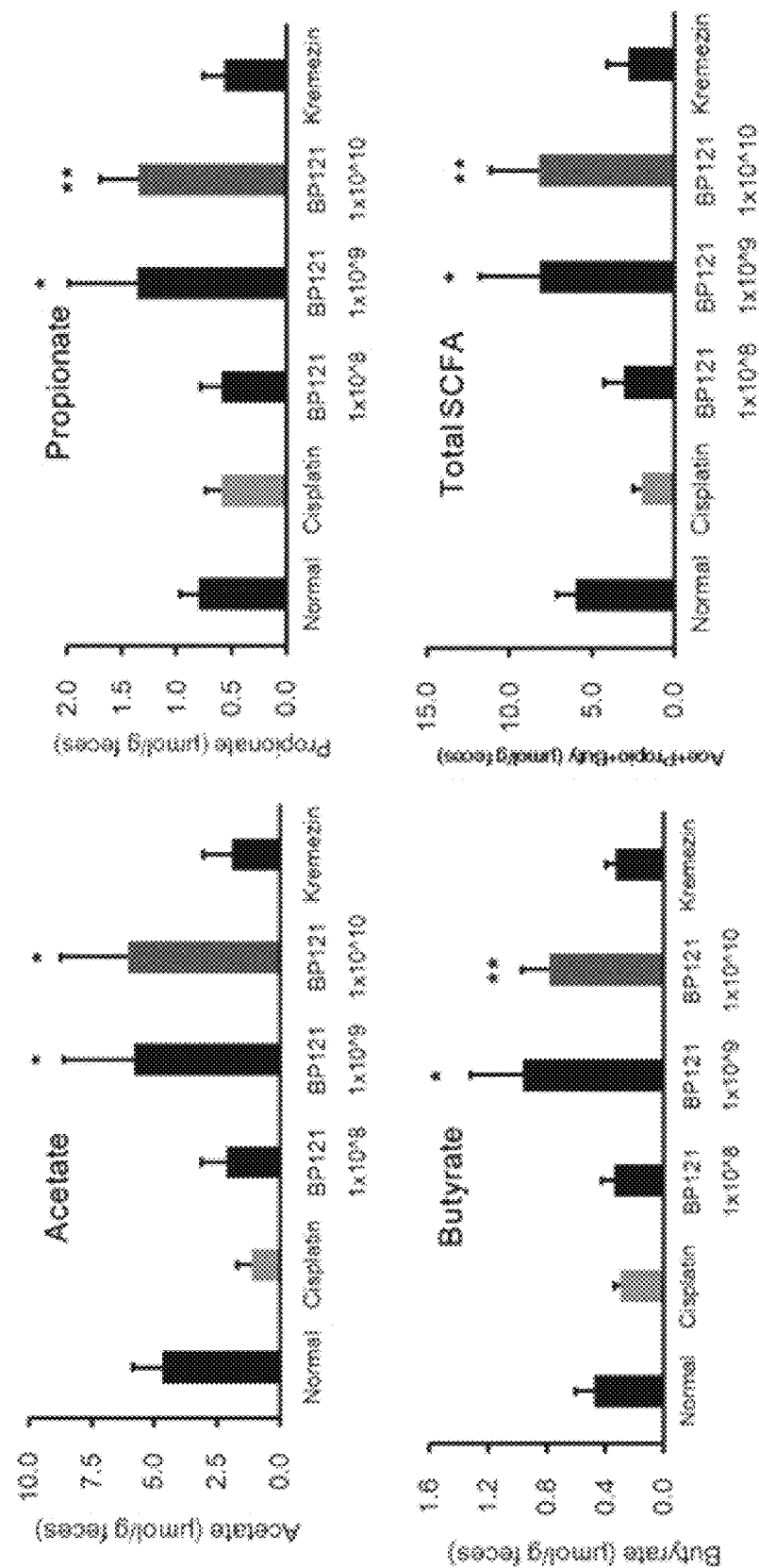
[Figure 8]

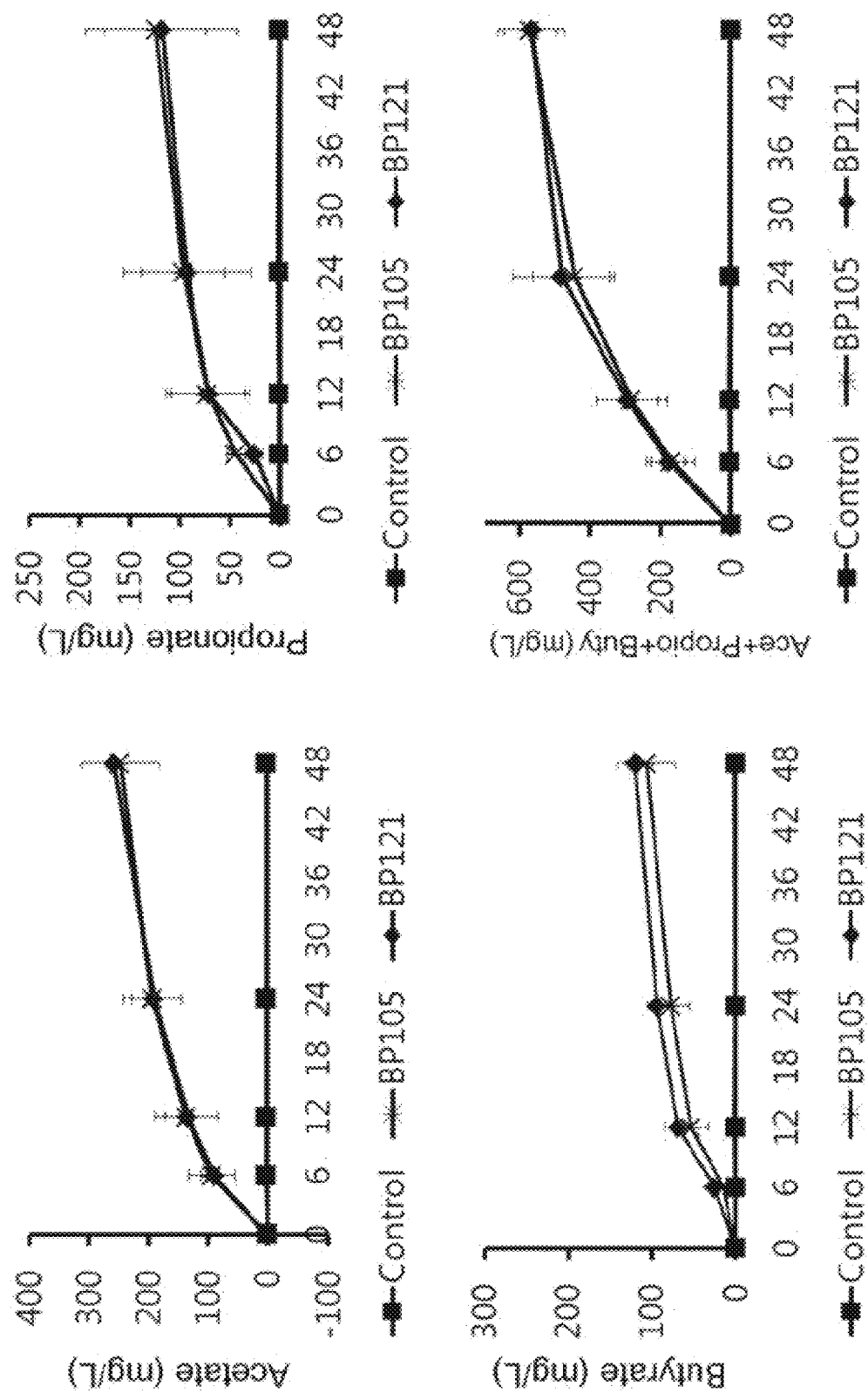
[Figure 9]

SEQUENCE LISTING

<160> NUMBER OF SEQ ID NOS: 2

<210> SEQ ID NO 1
<211> LENGTH: 1442
<212> TYPE: RNA
<213> ORGANISM: Artificial Sequence
<220> FEATURE:
<223> OTHER INFORMATION: 16S rRNA of bacterial strain, L. acidophilus
      BP105

<400> SEQUENCE: 1

| | | | | | | |
|---|---|---|---|---|---|---|
| ctcaggacga | acgctggcgg | cgtgcctaat | acatgcaagt | cgagcgagct | gaaccaacag | 60 |
| attcacttcg | gtgatgacgt | tgggaacgcg | agcggcggat | gggtgagtaa | cacgtgggga | 120 |
| acctgcccca | tagtctggga | taccacttgg | aaacaggtgc | taataccgga | taagaaagca | 180 |
| gatcgcatga | tcagcttata | aaaggcggcg | taagctgtcg | ctatgggatg | gccccgcggt | 240 |
| gcattagcta | gttggtaggg | taacggccta | ccaaggcaat | gatgcatagc | cgagttgaga | 300 |
| gactgatcgg | ccacattggg | actgagacac | ggcccaaact | cctacgggag | gcagcagtag | 360 |
| ggaatcttcc | acaatggacg | aaagtctgat | ggagcaacgc | cgcgtgagtg | aagaaggttt | 420 |
| tcggatcgta | aagctctgtt | gttggtgaag | aaggatagag | gtagtaactg | gcctttattt | 480 |
| gacggtaatc | aaccagaaag | tcacggctaa | ctacgtgcca | gcagccgcgg | taatacgtag | 540 |
| gtggcaagcg | ttgtccggat | ttattgggcg | taaagcgagc | gcaggcggaa | gaataagtct | 600 |
| gatgtgaaag | ccctcggctt | aaccgaggaa | ctgcatcgga | aactgttttt | cttgagtgca | 660 |
| gaagaggaga | gtggaactcc | atgtgtagcg | gtggaatgcg | tagatatatg | gaagaacacc | 720 |
| agtggcgaag | gcggctctct | ggtctgcaac | tgacgctgag | gctcgaaagc | atgggtagcg | 780 |
| aacaggatta | gataccctgg | tagtccatgc | cgtaaacgat | gagtgctaag | tgttgggagg | 840 |
| tttccgcctc | tcagtgctgc | agctaacgca | ttaagcactc | cgcctgggga | gtacgaccgc | 900 |
| aaggttgaaa | ctcaaaggaa | ttgacggggg | cccgcacaag | cggtggagca | tgtggtttaa | 960 |
| ttcgaagcaa | cgcgaagaac | cttaccaggt | cttgacatct | agtgcaatcc | gtagagatac | 1020 |
| ggagttccct | tcggggacac | taagacaggt | ggtgcatggc | tgtcgtcagc | tcgtgtcgtg | 1080 |
| agatgttggg | ttaagtcccg | caacgagcgc | aaccccttgtc | attagttgcc | agcattaagt | 1140 |
| tgggcactct | aatgagactg | ccggtgacaa | accggaggaa | ggtggggatg | acgtcaagtc | 1200 |
| atcatgcccc | ttatgacctg | ggctacacac | gtgctacaat | ggacagtaca | acgaggagca | 1260 |
| agcctgcgaa | ggcaagcgaa | tctcttaaag | ctgttctcag | ttcggactgc | agtctgcaac | 1320 |
| tcgactgcac | gaagctggaa | tcgctagtaa | tcgcggatca | gcacgccgcg | gtgaatacgt | 1380 |
| tcccgggcct | tgtacacacc | ggcccgtcac | accatgggaa | gtctgcaatg | ccccaaaccc | 1440 |
| gg | | | | | | 1442 |

<210> SEQ ID NO 2
<211> LENGTH: 1401
<212> TYPE: RNA
<213> ORGANISM: Artificial Sequence
<220> FEATURE:
<223> OTHER INFORMATION: 16S rRNA of bacterial strain, L.salivarius
      BP121

<400> SEQUENCE: 2

| | | | | | | |
|---|---|---|---|---|---|---|
| cctagatata | gttttttttaa | tgctcaggac | gaacgctggc | ggcgtgccta | atacatgcaa | 60 |
| gtcgaacgaa | actttcttac | accgaatgct | tgcattcatc | gtaagaagtt | gagtggcgga | 120 |
| cgggtgagta | acacgtgggt | aacctgccta | aaagaagggg | ataacacttg | gaaacaggtg | 180 |

```
ctaataccgt atatctctaa ggatcgcatg atccttagat gaaagatggt tctgctatcg    240
cttttagatg gacccgcggc gtattaacta gttggtgggg taacggccta ccaaggtgat    300
gatacgtagc cgaactgaga ggttgatcgg ccacattggg actgagacac ggcccaaact    360
cctacgggag gcagcagtag ggaatcttcc acaatggacg caagtctgat ggagcaacgc    420
cgcgtgagtg aagaaggtct tcggatcgta aaactctgtt gttagagaag aacacgagtg    480
agagtaactg ttcattcgat gacggtatct aaccagcaag tcacggctaa ctacgtgcca    540
gcagccgcgg taatacgtag gtggcaagcg ttgtccggat ttattgggcg taaagggaac    600
gcaggcggtc ttttaagtct gatgtgaaag ccttcggctt aaccggagta gtgcattgga    660
aactggaaga cttgagtgca gaagaggaga gtggaactcc atgtgtagcg gtgaaatgcg    720
tagatatatg gaagaacacc agtggcgaaa gcggctctct ggtctgtaac tgacgctgag    780
gttcgaaagc gtgggtagca aacaggatta gataccctgg tagtccacgc cgtaaacgat    840
gaatgctagg tgttggaggg tttccgccct tcagtgccgc agctaacgca ataagcattc    900
cgcctgggga gtacgaccgc aaggttgaaa ctcaaaggaa ttgacggggg cccgcacaag    960
cggtggagca tgtggtttaa ttcgaagcaa cgcgaagaac cttaccaggt cttgacatcc    1020
tttgaccacc taagagatta ggctttccct tcggggacaa agtgacaggt ggtgcatggc    1080
tgtcgtcagc tcgtgtcgtg agatgttggg ttaagtcccg caacgagcgc aacccttgtt    1140
gtcagttgcc agcattaagt tgggcactct ggcgagactg ccggtgacaa accggaggaa    1200
ggtggggacg acgtcaagtc atcatgcccc ttatgacctg ggctacacac gtgctacaat    1260
ggacggtaca acgagtcgcg agaccgcgag gtttagctaa tctcttaaag ccgttctcag    1320
ttcggattgt aggctgcaac tcgcctacat gaagtcggaa tcgctagtaa tcgcgaatca    1380
gcatgtcgcg gtgaatacgt t                                              1401
```

PROBIOTICS FOR INHIBITING AND PREVENTING PROGRESSION OF RENAL DISEASES, AND COMPOSITIONS FOR INHIBITING AND PREVENTING PROGRESSION OF RENAL DISEASES COMPRISING SAME

CROSS-REFERENCE TO RELATED APPLICATIONS

This application is a National Stage of International Application No. PCT/KR2018/015883 filed on Dec. 13, 2018, which claims priority under U.S.C. § 119(a) to Korean Patent Application No. 10-2017-0173590 filed on Dec. 15, 2017, the disclosure of which is incorporated herein in its entirety by reference.

TECHNICAL FIELD

The present invention relates to probiotics for inhibiting and preventing the progression of a renal disease and a composition for inhibiting and preventing the progression of a renal disease comprising the same; and a novel *Lactobacillus acidophilus* BP105 strain, a novel *Lactobacillus salivarius* BP121 strain, and a composition for inhibiting and preventing the progression of a renal disease comprising the same.

BACKGROUND ART

Due to the increase in the elderly population, the number of patients with adult diseases such as diabetes and hypertension is on the rise. These diabetes and hypertension are the most common causes of chronic renal failure, and the number of patients with chronic renal failure due to them is also rapidly increasing.

Chronic renal disease is increasing in prevalence rate worldwide, and is known to be a very serious disease with a prevalence rate of 14% in the United States and a prevalence rate of 10% in China. The number of patients with chronic renal disease in Korea is about 170,000 (2015), which is reported to have increased by 107% compared to 2008, and as of 2015, the medical expenses of patients related to chronic renal disease are also reported to amount to about KRW 1.56 trillion.

Chronic renal disease is an irreversible disease with no underlying treatment, and 90% of patients with chronic renal disease progress to end-stage renal failure. In the case of end-stage renal failure, hemodialysis, peritoneal dialysis, and kidney transplantation is performed as renal replacement therapy. Therefore, since it is important to inhibit the progression of renal failure at the beginning of symptoms, effective renal disease progression inhibitors and renal disease prevention agents are desired.

It is generally known that in the body of patients with renal failure, blood levels of uremic toxins such as indoxyl sulfate and p-cresol, which are renal failure progression factors or vascular dysfunction factors, are high, and blood creatinine levels and neutral fat levels, which are indicators of renal dysfunction, are elevated.

Among them, indoxyl sulfate and p-cresol have been reported as uremic toxins that have been proven to be renal failure progression factors, and the blood levels of indoxyl sulfate in patients with chronic renal failure are very high compared to those in healthy people.

Indoxyl sulfate is a substance that progresses and exacerbates a renal disease and causes cardiovascular disease and glomerulosclerosis as described above, and thus it is thought that by lowering the blood levels of indoxyl sulfate in patients with renal failure, the disability of renal function may be remarkably reduced and the progression of renal failure may be inhibited. On the other hand, uremic toxins such as indoxyl sulfate and p-cresol are substances that have high binding power with proteins and thus cannot be removed even by the renal replacement therapy.

Therefore, it is known that a spherical adsorptive carbon as a conventional renal failure progression inhibitor adsorbs indole, which is a precursor of indoxyl sulfate, in the intestinal tract, and excretes it in feces, thereby lowering the blood levels of indoxyl sulfate. As a result, in addition to inhibiting the progression of renal failure, it has been reported that the mortality due to the onset of cardiovascular diseases involved in renal failure was also lowered.

However, it has been confirmed that the spherical adsorptive carbon is not only that internal use is burdensome because of the need to take 6 g, or 30 capsules per day, but also that many patients want to stop taking medicine since symptoms such as abdominal distention and constipation are severe and its long-term internal use is accompanied by very large pain, as side effects.

For these reasons, there is a demand for a novel medicament that relieves the pain or burden of the patient with less dosage and without causing abdominal distention or constipation.

In addition, patients with chronic renal failure develop a hyperphosphatemia due to a phenomenon in which phosphorus discharge ability decreases and the blood phosphorus greatly increases. If the blood phosphorus increases, it stimulates the parathyroid gland to secrete parathyroid hormone in order to keep the ratio of calcium and phosphorus relatively, which releases calcium from the bones. If this phenomenon is maintained, more calcium is released from the bones, and the bone is weakened, and thus the quality of life rapidly decreases due to renal osteoporosis accompanied by osteoporosis. Therefore, in patients with chronic renal failure, managing the blood phosphorus concentration is directly related to the quality of life, and management is desired from the beginning of the disease.

The standard of the blood phosphorus concentration of healthy people is 5.5 mg/dL or less, and most patients with chronic renal failure are educated to eat foods with a low phosphorus content, and additionally take a phosphorus binding agent during meals to prevent the phosphorus in the food from being absorbed into the body. However, it is a reality that it is not easy to control the blood phosphorus concentration, so that only 40-50% of total hemodialysis patients have been reported to have achieved the target blood phosphorus concentration.

On the other hand, drugs for treating the increase in phosphorus in the blood include a calcium-based phosphorus binding agent, a drug in the form of replacing the phosphorus binding agent, and the like. Phosphorus binding agent, which is a drug that inhibits the rise in the blood phosphorus concentration by binding with phosphorus in food in the intestine and excreting it in feces, controls the blood phosphorus concentration, but has the disadvantages that the blood calcium concentration is increased, side effects such as dyspepsia and constipation are caused, and the drug price is expensive.

Probiotics-based drugs using a strain that absorbs phosphorus have been introduced as the drug in the form of replacing the phosphorus binding agent. However, studies of probiotics to remove uremic toxins are insufficient, and management of uremic toxins is the most important in inhibiting and preventing progression of renal disease. The probiotics-based drugs as introduced so far are in a state of insufficient reliability for effect and safety to replace other conventional drugs.

Therefore, it is an urgent situation to develop a safe and effective method of replacing existing spherical adsorptive carbon with large side effects, removing uremic toxins in the body, and discharging phosphorus.

PRIOR ART DOCUMENT

[Patent Document]
Korean Patent No. 10-1684289

DISCLOSURE

Technical Problem

The present invention has been devised to solve the above problems of the prior art, and its object is to provide probiotics for inhibiting and preventing the progression of a renal disease and a composition for inhibiting and preventing the progression of a renal disease comprising the same; and a novel *Lactobacillus acidophilus* BP105 strain, a novel *Lactobacillus salivarius* BP121 strain, and a composition for inhibiting and preventing the progression of a renal disease comprising the same, which are free from side effects such as dyspepsia and constipation, have excellent indoxyl sulfate removal ability, p-cresol removal ability, phosphorus absorption ability, and the like, and are safe for the human body.

Technical Solution

In order to solve the above problems, the present invention provides probiotics for inhibiting and preventing the progression of a renal disease, comprising a strain isolated from feces of infants by a method comprising the steps of:

(a) diluting feces of infants 12 months or less of age with sterile water and inoculating MRS medium with the feces to incubate them;

(b) subculturing a milky white single colony produced in the MRS medium; and (C) selecting and obtaining lactic acid bacteria from the colonies subcultured in step (b).

The probiotics are characterized by including one or more selected from a *Lactobacillus acidophilus* BP105 strain (Accession No. KCCM12169P) and a *Lactobacillus salivarius* BP121 strain (Accession No. KCCM12170P).

In addition, the present invention provides a composition for inhibiting and preventing the progression of a renal disease, comprising one or more selected from the groups consisting of the probiotics, cultures thereof, concentrates thereof, pastes thereof, spray-dried materials thereof, lyophilisates thereof, vacuum-dried materials thereof, drum-dried materials thereof, liquids thereof, dilutions thereof, and crushes thereof.

In addition, the present invention provides a *Lactobacillus acidophilus* BP105 strain (Accession No. KCCM12169P).

The strain is characterized by having excellent indoxyl sulfate removal ability, p-cresol removal ability, and phosphorus absorption ability.

In addition, the present invention provides a composition for inhibiting and preventing the progression of a renal disease, comprising one or more selected from the groups consisting of the *Lactobacillus acidophilus* BP105 strain, cultures thereof, concentrates thereof, pastes thereof, spray-dried materials thereof, lyophilisates thereof, vacuum-dried materials thereof, drum-dried materials thereof, liquids thereof, dilutions thereof, and crushes thereof.

In addition, the present invention provides a *Lactobacillus salivarius* BP121 strain (Accession No. KCCM12170P).

The strain is characterized by having excellent indoxyl sulfate removal ability, p-cresol removal ability, and phosphorus absorption ability.

In addition, the present invention provides a composition for inhibiting and preventing the progression of a renal disease, comprising one or more selected from the groups consisting of the *Lactobacillus salivarius* BP121 strain, cultures thereof, concentrates thereof, pastes thereof, spray-dried materials thereof, lyophilisates thereof, vacuum-dried materials thereof, drum-dried materials thereof, liquids thereof, dilutions thereof, and crushes thereof.

In addition, the present invention provides a method of treating an animal with a renal disease, comprising administering the following in an effective amount to an animal:

the probiotics, or the pharmaceutical composition comprising one or more selected from the groups consisting of the probiotics, cultures thereof, concentrates thereof, pastes thereof, spray-dried materials thereof, lyophilisates thereof, vacuum-dried materials thereof, drum-dried materials thereof, liquids thereof, dilutions thereof, and crushes thereof;

the *Lactobacillus acidophilus* BP105 strain (Accession No. KCCM12169P), or the pharmaceutical composition comprising one or more selected from the groups consisting of the *Lactobacillus acidophilus* BP105 strain, cultures thereof, concentrates thereof, pastes thereof, spray-dried materials thereof, lyophilisates thereof, vacuum-dried materials thereof, drum-dried materials thereof, liquids thereof, dilutions thereof, and crushes thereof; or the *Lactobacillus salivarius* BP121 strain (Accession No. KCCM12170P), or the pharmaceutical composition comprising one or more selected from the groups consisting of the *Lactobacillus salivarius* BP121 strain, cultures thereof, concentrates thereof, pastes thereof, spray-dried materials thereof, lyophilisates thereof, vacuum-dried materials thereof, drum-dried materials thereof, liquids thereof, dilutions thereof, and crushes thereof.

Advantageous Effects

The probiotics for inhibiting and preventing the progression of a renal disease according to the present invention are free from side effects such as dyspepsia and constipation, have excellent indoxyl sulfate removal ability, p-cresol removal ability, phosphorus absorption ability, and the like, and are safe for the human body, and thus provide a very excellent effect on inhibiting and preventing the progression of a renal disease.

In addition, novel *Lactobacillus acidophilus* BP105 strain and *Lactobacillus salivarius* BP121 strain according to the present invention are free from side effects such as dyspepsia and constipation, have excellent indoxyl sulfate removal ability, p-cresol removal ability, phosphorus absorption ability, and the like, and are safe for the human body, and thus provide a very excellent effect on inhibiting and preventing the progression of a renal disease.

In addition, a composition for inhibiting and preventing the progression of a renal disease comprising the probiotics, the novel *Lactobacillus acidophilus* BP105 strain, or the novel *Lactobacillus salivarius* BP121 strain according to the present invention is free from side effects such as dyspepsia and constipation, has excellent indoxyl sulfate removal ability, p-cresol removal ability, phosphorus absorption ability, and the like, and is safe for the human body, and thus provides a very excellent effect on inhibiting and preventing the progression of a renal disease.

BRIEF DESCRIPTION OF DRAWINGS

FIG. 1 is a photograph showing the photographed results of the phosphorus absorption test of the *Lactobacillus acidophilus* BP105 strain (B) and the *Lactobacillus salivarius* BP121 strain (C), carried out in Test Example 3.

FIG. 2 is a graph showing the measured results of the phosphorus absorption rate per hour for each strain of the *Lactobacillus acidophilus* BP105 strain and the *Lactobacillus salivarius* BP121 strain in Test Example 4.

FIG. 3 is a graph showing the measured results of phosphorus absorption rate while incubating the *Lactobacillus acidophilus* BP105 strain for 9 hours in Test Example 4.

FIG. 4 is a graph showing the measured results of phosphorus absorption rate while incubating the *Lactobacillus salivarius* BP121 strain for 9 hours in Test Example 4.

FIG. 5 is a graph showing the evaluated results of the indoxyl sulfate inhibitory efficacy of the *Lactobacillus acidophilus* BP105 strain, the *Lactobacillus salivarius* BP121 strain, and mixtures thereof, using cisplatin intraperitoneally administered male rats (SD rats) as an acute renal disease model in Test Example 5.

FIGS. 6 and 7 are graphs showing the evaluated results of the renal protective efficacy of the *Lactobacillus salivarius* BP121 strain, using cisplatin intraperitoneally administered male rats (SD rats) as an acute renal disease model in Test Example 6.

FIG. 8 is a graph showing the results confirmed by using the feces for changes in the body of short-chain fatty acids by administration of the *Lactobacillus salivarius* BP121 strain, using cisplatin intraperitoneally administered male rats (SD rats) as an acute renal disease model in Test Example 6.

FIG. 9 is a graph showing the measured results of the amount of short-chain fatty acids over time through a single culture of the *Lactobacillus acidophilus* BP105 strain and the *Lactobacillus salivarius* BP121 strain in Test Example 7, in order to verify whether the change in the amount of short-chain fatty acids by administration of the *Lactobacillus salivarius* BP121 strain (Test Example 6) is an effect of BP121 administration.

BEST MODE

Hereinafter, the present invention will be described in more detail.

Unless defined otherwise, all technical terms used in the present invention have the same meaning as commonly understood by those skilled in the art in the relevant field of the present invention. In addition, preferred methods or samples are described in the present specification, but similar or equivalent ones are included in the scope of the present invention. The contents of all publications described by reference in the present specification are incorporated in the present specification by reference in their entirety.

The present invention relates to probiotics for inhibiting and preventing the progression of a renal disease, comprising a strain isolated from human feces, preferably feces of infants by a method comprising the steps of:

(a) diluting feces of infants 12 months or less of age with sterile water and inoculating MRS medium with the feces to incubate them;

(b) subculturing a milky white single colony produced in the MRS medium; and (C) selecting and obtaining lactic acid bacteria from the colonies subcultured in step (b).

The probiotics include 15 strains as shown in Table 1 below:

TABLE 1

| Identified Strains |
| --- |
| BP101 |
| BP103 |
| BP104 |
| BP105 |
| BP107 |
| BP109 |
| BP110 |
| BP111 |
| BP115 |
| BP121 |
| BP122 |
| BP123 |
| BP131 |
| BP132 |
| BP133 |

The strains were identified by 16s rRNA analysis of the probiotics of the present invention.

In particular, the probiotics are characterized by including a *Lactobacillus acidophilus* BP105 strain deposited under Accession No. KCCM12169P and *Lactobacillus salivarius* BP121 deposited under Accession No. KCCM12170P.

The novel strains, the *Lactobacillus acidophilus* BP105 strain and the *Lactobacillus salivarius* BP121 strain were deposited, according to the provisions of the Budapest Treaty on the International Recognition of the Deposit of Microorganisms for the Purposes of Patent Procedure, with the Korean Culture Center of Microorganisms on Nov. 16, 2017 under the names as described above. The accession numbers are KCCM12169P for *Lactobacillus acidophilus* BP105 and KCCM12170P for *Lactobacillus salivarius* BP121. Korean Culture Center of Microorganisms is located at the following address: Yurim B/D, 45 Hongjenae 2ga-gil, Hongje-dong, Seodaemun-gu, Seoul 120-861, South Korea.

Each of the 15 strains exhibits excellent effects on indoxyl sulfate removal and p-cresol removal. In particular, the *Lactobacillus acidophilus* BP105 strain and the *Lactobacillus salivarius* BP121 strain exhibit very excellent effects on indoxyl sulfate removal and p-cresol removal, and also exhibit very excellent effects on phosphorus absorption rate.

The probiotics of the present invention which may be used have, but are not limited to, a live bacteria content of $1 \times 10^1$ to $1 \times 10^{15}$ CFU/g.

In addition, the present invention relates to a composition for inhibiting and preventing the progression of a renal disease, comprising one or more selected from the groups consisting of the probiotics, cultures thereof, concentrates thereof, pastes thereof, spray-dried materials thereof, lyophilisates thereof, vacuum-dried materials thereof, drum-dried materials thereof, liquids thereof, dilutions thereof, and crushes thereof.

The composition for inhibiting and preventing the progression of a renal disease may be a pharmaceutical composition or a food composition.

The pharmaceutical composition may be granules, limonades, powders, syrups, liquids and solutions, extracts, elixirs, fluid extracts, suspensions, decoctions, infusions, tablets, spirits, capsules, troches, pills, or soft or hard gelatin capsules.

The type of the food composition is not particularly limited, and includes a general food composition as well as a health functional food composition.

In addition, the present invention relates to a *Lactobacillus acidophilus* BP105 strain deposited under Accession No. KCCM12169P.

The strain has excellent indoxyl sulfate removal ability, p-cresol removal ability, and phosphorus absorption ability.

In addition, the present invention relates to a composition for inhibiting and preventing the progression of a renal disease, comprising one or more selected from the groups consisting of the *Lactobacillus acidophilus* BP105 strain, cultures thereof, concentrates thereof, pastes thereof, spray-dried materials thereof, lyophilisates thereof, vacuum-dried materials thereof, drum-dried materials thereof, liquids thereof, dilutions thereof, and crushes thereof.

The composition for inhibiting and preventing the progression of a renal disease may be a pharmaceutical composition or a food composition.

The pharmaceutical composition may be granules, limonades, powders, syrups, liquids and solutions, extracts, elixirs, fluid extracts, suspensions, decoctions, infusions, tablets, spirits, capsules, troches, pills, or soft or hard gelatin capsules.

The type of the food composition is not particularly limited, and includes a general food composition as well as a health functional food composition.

In addition, the present invention relates to a *Lactobacillus salivarius* BP121 strain deposited under Accession No. KCCM12170P.

The strain has excellent indoxyl sulfate removal ability, p-cresol removal ability, and phosphorus absorption ability.

In addition, the present invention relates to a composition for inhibiting and preventing the progression of a renal disease, comprising one or more selected from the groups consisting of the *Lactobacillus salivarius* BP121 strain, cultures thereof, concentrates thereof, pastes thereof, spray-dried materials thereof, lyophilisates thereof, vacuum-dried materials thereof, drum-dried materials thereof, liquids thereof, dilutions thereof, and crushes thereof.

The composition for inhibiting and preventing the progression of a renal disease may be a pharmaceutical composition or a food composition.

The form of the pharmaceutical composition may be granules, limonades, powders, syrups, liquids and solutions, extracts, elixirs, fluid extracts, suspensions, decoctions, infusions, tablets, spirits, capsules, troches, pills, or soft or hard gelatin capsules, but is not limited thereto.

The type of the food composition is not particularly limited, and includes a general food composition as well as a health functional food composition.

In the present invention, the pharmaceutical composition as described above may further comprise a pharmaceutically acceptable carrier. The pharmaceutically acceptable carriers comprised in the pharmaceutical composition of the present invention are those conventionally used in the formulation and include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, mineral oil, and the like.

The pharmaceutical composition of the present invention may further comprise a lubricant, a wetting agent, a sweetener, a flavoring agent, an emulsifier, a suspending agent, a preservative, and the like, in addition to the ingredients as described above.

The pharmaceutical composition of the present invention may be administered orally or parenterally.

The pharmaceutical composition of the present invention may be formulated in a single-dose form or in multi-dose vessels using a pharmaceutically acceptable carrier and/or excipient, according to a method that may be easily carried out by those skilled in the art.

In the present invention, the food composition as described above may comprise, in addition to the active ingredient, ingredients that are commonly added during food preparation, and, for example, may comprise proteins, carbohydrates, fats, nutrients, seasonings, sweeteners and flavoring agents, but is not limited thereto. Examples of the carbohydrates include conventional sugars, such as monosaccharides, for example, glucose, fructose, and the like; disaccharides, for example, maltose, sucrose, oligosaccharide, and the like; and polysaccharides, for example, dextrin, cyclodextrin, and the like, and sugar alcohols such as xylitol, sorbitol, and erythritol. As the sweeteners, natural sweeteners (taumatin, stevia extract, rebaudioside A, glycyrrhizin, and the like) and synthetic sweeteners (saccharin, aspartame, and the like) may be used.

Examples of the food composition may include patient nutrition, meat, cereals, caffeine drinks, general drinks, dairy products, chocolates, bread, snacks, confectionery, pizza, jelly, noodles, gums, ice cream, alcoholic beverages, alcohols, vitamin complexes, other health supplement foods, and the like, but are not limited thereto. When prepared in the form of the food composition as described above, it is preferable because patients suffering from diseases caused by an increase in uremic toxins in the blood and an increase in the concentration of phosphorus in the blood may take it conveniently and easily.

In the present invention, the dosage of the probiotics, *Lactobacillus acidophilus* BP105 strain and *Lactobacillus salivarius* BP121 strain is preferably determined in consideration of the administration method, the age, sex, body weight and severity of the disease of the patient, and the like.

By way of an embodiment, the probiotics, *Lactobacillus acidophilus* BP105 strain and *Lactobacillus salivarius* BP121 strain may be administered with a living bacteria content of $1 \times 10^1$ to $1 \times 10^{15}$ CFU/g per day and it can be administered in more than once a day.

In addition, the pharmaceutical composition or the food composition comprising the above ingredients may be administered one or more times per day with a living bacteria content of $1 \times 10^1$ to $1 \times 10^{15}$ CFU/g, based on the active ingredients.

However, the above dosage is only an example, and may be changed by a doctor's prescription according to the patient's condition.

MODE FOR CARRYING OUT THE INVENTION

Hereinafter, the present invention will be described in detail by way of the following examples. However, the following examples are only for illustrating the present invention, and the scope of the present invention is not limited to the following examples.

Example 1: Isolation of Probiotics

The feces of infants of 1 month of age were diluted 10 steps in sterile water to isolate the strains by the dilution plating method. The diluted fecal sample was smeared into MRS medium (MRS broth agar; BD Difco), and then incubated anaerobically at 37° C. for 72 hours. A milky white single colony appearing on the MRS agar plate was subcultured to purely isolate the probiotics of the present invention.

Example 2: Identification of Strains Included in Probiotics

Chromosomal DNA extraction and purification were performed on the strain purely isolated in Example 1 above. Two universal primers, 27F (5'-AGAGTTT-GATCMTGGCTCAG-3') and 1492R (5'-TACG-GYTACCTTGTTACGACTT-3') were used to perform amplification of the 16s rRNA gene, and then sequencing analysis of the amplified 16s rRNA gene was performed. Using the analyzed 16s rRNA sequence data and EzTaxon server (http://www.ezbiocloud.net), only 15 strains corresponding to GRAS (Generally Recognized as Safe) were selected and shown in Table 2 below.

TABLE 2

| Identified Strains |
| --- |
| BP101 |
| BP103 |
| BP104 |
| BP105 |
| BP107 |
| BP109 |
| BP110 |
| BP111 |
| BP115 |
| BP121 |
| BP122 |
| BP123 |
| BP131 |
| BP132 |
| BP133 |

The results of 16S rRNA sequencing analysis for BP105—*L. acidophilus* were as follows:

<16S rRNA of bacterial strain, *L. acidophilus* BP105>
(SEQ ID NO: 1)
CTCAGGACGAACGCTGGCGGCGTGCCTAATACATGCAAGTCGAGCGAGCT

GAACCAACAGATTCACTTCGGTGATGACGTTGGGAACGCGAGCGGCGGAT

GGGTGAGTAACACGTGGGGAACCTGCCCCATAGTCTGGGATACCACTTGG

AAACAGGTGCTAATACCGGATAAGAAAGCAGATCGCATGATCAGCTTATA

AAAGGCGGCGTAAGCTGTCGCTATGGGATGGCCCCGCGGTGCATTAGCTA

GTTGGTAGGGTAACGGCCTACCAAGGCAATGATGCATAGCCGAGTTGAGA

GACTGATCGGCCACATTGGGACTGAGACACGGCCCAAACTCCTACGGGAG

GCAGCAGTAGGGAATCTTCCACAATGGACGAAAGTCTGATGGAGCAACGC

CGCGTGAGTGAAGAAGGTTTTCGGATCGTAAAGCTCTGTTGTTGGTGAAG

AAGGATAGAGGTAGTAACTGGCCTTTATTTGACGGTAATCAACCAGAAAG

TCACGGCTAACTACGTGCCAGCAGCCGCGGTAATACGTAGGTGGCAAGCG

TTGTCCGGATTTATTGGGCGTAAAGCGAGCGCAGGCGGAAGAATAAGTCT

GATGTGAAAGCCCTCGGCTTAACCGAGGAACTGCATCGGAAACTGTTTTT

CTTGAGTGCAGAAGAGGAGAGTGGAACTCCATGTGTAGCGGTGGAATGCG

TAGATATATGGAAGAACACCAGTGGCGAAGGCGGCTCTCTGGTCTGCAAC

TGACGCTGAGGCTCGAAAGCATGGGTAGCGAACAGGATTAGATACCCTGG

TAGTCCATGCCGTAAACGATGAGTGCTAAGTGTTGGGAGGTTTCCGCCTC

TCAGTGCTGCAGCTAACGCATTAAGCACTCCGCCTGGGGAGTACGACCGC

AAGGTTGAAACTCAAAGGAATTGACGGGGGCCCGCACAAGCGGTGGAGCA

TGTGGTTTAATTCGAAGCAACGCGAAGAACCTTACCAGGTCTTGACATCT

AGTGCAATCCGTAGAGATACGGAGTTCCCTTCGGGGACACTAAGACAGGT

GGTGCATGGCTGTCGTCAGCTCGTGTCGTGAGATGTTGGGTTAAGTCCCG

CAACGAGCGCAACCCTTGTCATTAGTTGCCAGCATTAAGTTGGGCACTCT

AATGAGACTGCCGGTGACAAACCGGAGGAAGGTGGGGATGACGTCAAGTC

ATCATGCCCCTTATGACCTGGGCTACACACGTGCTACAATGGACAGTACA

ACGAGGAGCAAGCCTGCGAAGGCAAGCGAATCTCTTAAAGCTGTTCTCAG

TTCGGACTGCAGTCTGCAACTCGACTGCACGAAGCTGGAATCGCTAGTAA

TCGCGGATCAGCACGCCGCGGTGAATACGTTCCCGGGCCTTGTACACACC

GGCCCGTCACACCATGGGAAGTCTGCAATGCCCCAAACCCGG

The results of 16S rRNA sequencing analysis for BP121—*L. salivarius* were as follows:

<16S rRNA of bacterial strain, *L. salivarius* BP121>
(SEQ ID NO: 2)
CCTAGATATAGTTTTTTTAATGCTCAGGACGAACGCTGGCGGCGTGCCTA

ATACATGCAAGTCGAACGAAACTTTCTTACACCGAATGCTTGCATTCATC

GTAAGAAGTTGAGTGGCGGACGGGTGAGTAACACGTGGGTAACCTGCCTA

AAAGAAGGGGATAACACTTGGAAACAGGTGCTAATACCGTATATCTCTAA

GGATCGCATGATCCTTAGATGAAAGATGGTTCTGCTATCGCTTTTAGATG

GACCCGCGGCGTATTAACTAGTTGGTGGGGTAACGGCCTACCAAGGTGAT

GATACGTAGCCGAACTGAGAGGTTGATCGGCCACATTGGGACTGAGACAC

GGCCCAAACTCCTACGGGAGGCAGCAGTAGGGAATCTTCCACAATGGACG

CAAGTCTGATGGAGCAACGCCGCGTGAGTGAAGAAGGTCTTCGGATCGTA

AAACTCTGTTGTTAGAGAAGAACACGAGTGAGAGTAACTGTTCATTCGAT

GACGGTATCTAACCAGCAAGTCACGGCTAACTACGTGCCAGCAGCCGCGG

TAATACGTAGGTGGCAAGCGTTGTCCGGATTTATTGGGCGTAAAGGGAAC

GCAGGCGGTCTTTTAAGTCTGATGTGAAAGCCTTCGGCTTAACCGGAGTA

GTGCATTGGAAACTGGAAGACTTGAGTGCAGAAGAGGAGAGTGGAACTCC

ATGTGTAGCGGTGAAATGCGTAGATATATGGAAGAACACCAGTGGCGAAA

GCGGCTCTCTGGTCTGTAACTGACGCTGAGGTTCGAAAGCGTGGGTAGCA

AACAGGATTAGATACCCTGGTAGTCCACGCCGTAAACGATGAATGCTAGG

TGTTGGAGGGTTTCCGCCCTTCAGTGCCGCAGCTAACGCAATAAGCATTC

CGCCTGGGGAGTACGACCGCAAGGTTGAAACTCAAAGGAATTGACGGGGG

CCCGCACAAGCGGTGGAGCATGTGGTTTAATTCGAAGCAACGCGAAGAAC

CTTACCAGGTCTTGACATCCTTTGACCACCTAAGAGATTAGGCTTTCCCT

-continued

TCGGGGACAAAGTGACAGGTGGTGCATGGCTGTCGTCAGCTCGTGTCGTG

AGATGTTGGGTTAAGTCCCGCAACGAGCGCAACCCTTGTTGTCAGTTGCC

AGCATTAAGTTGGGCACTCTGGCGAGACTGCCGGTGACAAACCGGAGGAA

GGTGGGGACGACGTCAAGTCATCATGCCCCTTATGACCTGGGCTACACAC

GTGCTACAATGGACGGTACAACGAGTCGCGAGACCGCGAGGTTTAGCTAA

TCTCTTAAAGCCGTTCTCAGTTCGGATTGTAGGCTGCAACTCGCCTACAT

GAAGTCGGAATCGCTAGTAATCGCGAATCAGCATGTCGCGGTGAATACGT

T

Test Example 1: Evaluation of Indoxyl Sulfate Removal Ability

To isolate microorganisms that remove and degrade indoxyl sulfate, which is known to cause oxidative stress in the kidney, the indoxyl sulfate removal ability was evaluated on 15 strains isolated in Example 2 above. After pre-incubation for 24 hours each in MRS broth, each 1% was inoculated in MRS broth to which indoxyl sulfate at a concentration of 60 μg/ml was added, and incubated for 24, 48, and 72 hours.

After obtaining the bacteria incubated for 24, 48, and 72 hours, respectively, centrifugation was performed at 12,000 rpm for 10 minutes to take the supernatant from which the bacteria were removed. Indican assay (Sigma Co., Ltd.) was used to measure residual indoxyl sulfate in the culture supernatant from which the bacteria were removed.

The measured results of residual indoxyl sulfate in the culture supernatant from which the bacteria were removed were shown in Table 3 below:

TABLE 3

| Strains | Removing Rate (%) of Indoxyl Sulfate Incubation (hrs) | | |
|---|---|---|---|
| | 24 | 48 | 72 |
| BP101 | 2.3 ± 2.4 | 10.3 ± 0.9 | 16.9 ± 1.6 |
| BP103 | 7.3 ± 1.8 | 8.3 ± 2.0 | 15.1 ± 7.7 |
| BP104 | 0.4 ± 0.2 | 3.3 ± 0.5 | 7.9 ± 2.4 |
| BP105 | 8.1 ± 1.9 | 21.2 ± 6.2 | 27.9 ± 4.4 |
| BP107 | 2.8 ± 0.7 | 8.3 ± 1.4 | 15.9 ± 1.3 |
| BP109 | −4.3 ± 0.9 | 1.4 ± 1.9 | 9.4 ± 2.0 |
| BP110 | −6.4 ± 1.4 | 0.5 ± 3.5 | 6.6 ± 1.7 |
| BP111 | 7.9 ± 2.3 | 11.0 ± 0.7 | 21.1 ± 3.2 |
| BP115 | 2.1 ± 3.0 | 11.1 ± 1.0 | 15.7 ± 1.7 |
| BP121 | 14.7 ± 0.9 | 24.7 ± 0.6 | 30.1 ± 0.5 |
| BP122 | 6.3 ± 0.8 | 11.9 ± 0.8 | 19.3 ± 1.3 |
| BP123 | 6.4 ± 0.2 | 12.7 ± 1.3 | 18.5 ± 1.6 |
| BP131 | 2.7 ± 1.0 | 10.9 ± 1.3 | 17.1 ± 1.1 |
| BP132 | 5.4 ± 2.3 | 10.9 ± 0.9 | 19.0 ± 1.7 |
| BP133 | 7.6 ± 1.1 | 9.9 ± 1.1 | 18.6 ± 5.3 |

As confirmed in Table 3 above, as a result of analyzing indoxyl sulfate in the culture supernatant taken by time, significant reduction in indoxyl sulfate when incubated for 24 hours was confirmed in 7 strains out of 15 strains compared to the medium that was not inoculated with bacteria. In particular, when incubated for 72 hours, it was confirmed that the *Lactobacillus acidophilus* BP105 strain removed 27.9±4.4% of indoxyl sulfate, and the *Lactobacillus salivarius* BP121 strain removed 30.1±0.5% of indoxyl sulfate, which was relatively superior.

Test Example 2: Evaluation of p-Cresol Removal Ability

To select for microorganisms that remove and decompose p-cresol known to cause cardiovascular disease, 15 microorganisms isolated in Example 2 above were pre-incubated in each MRS broth. 1% of the pre-incubated microorganisms were incubated for 24, 48, and 72 hours in MRS broth to which p-cresol at a concentration of 250 μg/ml was added.

After incubation for 24, 48, and 72 hours, respectively, a culture solution for each time was obtained and centrifugation was performed at 12,000 rpm for 10 minutes. To take the supernatant of the centrifuged bacteria and measure the amount of residual p-cresol, high-performance liquid chromatography (HPLC) analysis was performed. Prior to high performance liquid chromatography (HPLC) analysis, all samples were pretreated through a 0.22 μm filter (Millipore). The high performance liquid chromatography (HPLC) used in this experiment was a Waters Alliance e2695 system, and analysis was performed using a Phenomenex kintex C18 (5 μm, 4.6×250 mm) column. At this time, a UV detector (220 nm) was used as a detector, and analysis was performed under isocratical elution of a mobile phase using acetonitrile (ACN) 30%, a flow rate of 1 ml/min, and a column temperature of 35° C., and the results were shown in Table 4 below.

TABLE 4

| Strains | Removing Rate (%) of p-Cresol Incubation (hrs) | | |
|---|---|---|---|
| | 24 | 48 | 72 |
| BP101 | 1.90 ± 1.05 | 2.45 ± 0.27 | 4.37 ± 1.64 |
| BP103 | 2.93 ± 1.23 | 3.38 ± 1.51 | 2.40 ± 1.87 |
| BP104 | 0.92 ± 1.97 | 1.66 ± 1.44 | 3.26 ± 2.10 |
| BP105 | 3.62 ± 1.80 | 2.56 ± 2.57 | 3.03 ± 1.40 |
| BP107 | 1.46 ± 1.69 | 2.12 ± 0.87 | 1.90 ± 1.47 |
| BP109 | 2.74 ± 2.03 | 2.22 ± 0.97 | 3.08 ± 1.33 |
| BP110 | 2.95 ± 4.24 | 3.18 ± 0.54 | 2.83 ± 0.88 |
| BP111 | 0.42 ± 0.81 | 1.86 ± 0.68 | 1.57 ± 0.27 |
| BP115 | 0.60 ± 1.77 | 3.73 ± 1.40 | 3.12 ± 1.55 |
| BP121 | 4.70 ± 0.43 | 5.40 ± 1.96 | 5.89 ± 1.24 |
| BP122 | 1.37 ± 0.71 | 3.92 ± 1.40 | 2.96 ± 2.27 |
| BP123 | 4.54 ± 0.99 | 3.61 ± 1.19 | 3.42 ± 2.41 |
| BP131 | 8.80 ± 2.57 | 9.01 ± 0.18 | 9.06 ± 0.23 |
| BP132 | 0.66 ± 4.93 | 4.57 ± 2.49 | 2.43 ± 1.22 |
| BP133 | 0.74 ± 0.16 | 1.06 ± 0.91 | 2.38 ± 0.45 |

As confirmed in Table 3 above, as a result of analyzing the residual p-cresol in the culture supernatant for each time, significant reduction when incubated for 24 hours was shown in total 6 strains of BP101, BP103, BP105, BP121, BP123, and BP131 compared to the medium that was not inoculated with bacteria. In particular, when cultured up to 72 hours, it was confirmed that the *Lactobacillus* BP121 strain reduced 5.89±1.24% of p-cresol, and the *Lactobacillus* BP131 strain decreased 9.06±0.23% of p-cresol, which was relatively superior.

Test Example 3: Measurement of Phosphorus Absorption Rate

The *Lactobacillus acidophilus* BP105 strain (Accession No. KCCM12169P) and the *Lactobacillus salivarius* BP121 strain (Accession No. KCCM12170P), which are strains that have been confirmed to have indoxyl sulfate inhibitory ability and p-cresol inhibitory ability, were evaluated for their phosphorus absorption ability, which causes hyperphosphatemia when renal function decreases. The phosphorus absorption ability of microorganisms was carried out according to the colorimetric method using 5-bromo-4-chloro-3-indolyl phosphate disodium salt (Sigma Co., Ltd.). According to the colorimetric method, in the case of microorganisms using phosphate for growth, it shows a blue-green color. The experimental results are shown in FIG. 1.

As confirmed in FIG. 1, in the case of BP109 (A), the strain did not absorb phosphorus, and thus the color did not change and showed a milky white colony. On the other hand, strains of the *Lactobacillus acidophilus* BP105 strain (B) (Accession No. KCCM12169P) and the *Lactobacillus salivarius* BP121 strain (C) (Accession No. KCCM12170P) showed a blue-green color, and thus they were confirmed to absorb and use phosphorus.

Test Example 4: Evaluation of Phosphorus Absorption Rate (1) Measurement of Phosphorus Absorption Rate Per Strain To quantitatively evaluate the phosphorus absorption ability confirmed in Test Example 3, the phosphorus absorption rate for each strain was evaluated. Each of *Lactobacillus acidophilus* BP105 (Accession No. KCCM12169P) and *Lactobacillus salivarius* BP121 (Accession No. KCCM12170P) strains was pre-incubated in MRS broth, and then was inoculated with MRS medium containing 20 mM phosphate to have an OD value of 1.0.

First, the incubation is performed for 3 hours to measure the phosphorus absorption amount of the strain, and after 3 hours of incubation, the OD value was measured to derive the phosphorus absorption rate per strain by dividing the phosphorus absorption amount by the difference value (corresponding to the number of strains) from the original OD value. The phosphorus absorption amount was measured using Cedex Bio (Roche).

As a result of the experiment, the *Lactobacillus acidophilus* BP105 strain (Accession No. KCCM12169P) showed a phosphorus absorption rate of 0.0955 mM per hour, and the *Lactobacillus salivarius* BP121 strain (Accession No. KCCM12170P) showed a phosphorus absorption rate of 0.2384 mM per hour. As a result of the experiment, it was confirmed that the BP121 strain has a 2.5 times higher phosphorus absorption ability than the BP105 strain (see FIG. 2).

(2) Evaluation of Phosphorus Absorption Rate Over Time

To measure the phosphorus absorption rate over time of *Lactobacillus acidophilus* BP105 (Accession No. KCCM12169P) and *Lactobacillus salivarius* BP121 (Accession No. KCCM12170P), the strains were incubated for 9 hours in the same manner as above. As a result, it was confirmed that the BP105 strain absorbed 1.63 mM phosphorus until 9 hours (see FIG. 3), and the BP121 strain absorbed 3.51 mM phosphorus (see FIG. 4).

Test Example 5: Evaluation of Indoxyl Sulfate Inhibitory Efficacy in Acute Renal Disease Model Acute renal disease model was established by intraperitoneal administration of 7 mg/kg cisplatin to male rats (SD rats). $1\times10^9$ CFU of each of *Lactobacillus acidophilus* BP105 strain (Accession No. KCCM12169P and *Lactobacillus salivarius* BP121 strain (Accession No. KCCM12170P), and a mixture prepared at a concentration of $1\times10^9$ CFU by mixing both strains at a ratio of 1:1 were orally administered 10 days before induction and 4 days after induction of cisplatin, for a total of 14 days. The experiment was conducted for 2 weeks, and experimental animals were sacrificed on the $14^{th}$ day. To evaluate in vivo indoxyl sulfate inhibitory efficacy of BP105 and BP121 by inducing acute nephrotoxicity with cisplatin, the final blood indoxyl sulfate concentration was measured on the $14^{th}$ day. As a result, the groups administered with BP105, BP121, and mixtures thereof all showed a significant decrease in indoxyl sulfate compared to the acute nephrotoxicity-inducing group (see FIG. 5).

Test Example 6: Evaluation of Renal Protective Efficacy in Acute Renal Disease Model To evaluate the renal protective effect of the *Lactobacillus salivarius* BP121 strain (Accession No. KCCM12170P), male rats (SD rats) were intraperitoneally administered with 7 mg/kg cisplatin to induce acute renal disease, and then were evaluated for renal function. BP121 was administered in 3 groups of $1\times10^8$, $1\times10^9$, and $1\times10^{10}$ CFU, respectively, and Kremezin, a uremic agent, was administered orally at 0.5 g/rat as a positive control. Each group was administered orally 10 days before induction and 4 days after induction of cisplatin, for a total of 14 days, and the same amount of PBS was used in the control group.

To evaluate the renal protective effect, the concentrations of blood urea nitrogen (BUN) and creatinine, which are the renal function indicators, were measured. As a result, it was confirmed that in the high concentration of BP121-administered group, BUN decreased by 26% and creatinine decreased by 32%, all of which had significant efficacy. As a result of evaluating the concentration of indoxyl sulfate in the blood, it was confirmed to have a significant decrease of about 26%, but did not reach the uremic agent cremezin, which was confirmed by a 38% reduction (see FIG. 6).

As a result of confirming the inflammation indicator according to the administration of BP121 in blood and renal tissue, respectively, serum TNF-α decreased by 37% in the blood, showing a tendency to decrease, and decreased by 32% in the renal tissue, showing a significance. As a result of confirming the expression level of the inflammatory cytokine IL-6, a 26% reduction in serum and a 41% of marked reduction in renal tissue were confirmed compared to cisplatin-induced acute nephrotoxicity model. Malondialdehyde is a final product of lipid peroxidation, and its amount is significantly increased due to cisplatin administration, whereas the high concentration of BP121-administered group shows a significant tendency to decrease by 41%, confirming that the administration of BP121 plays an antioxidant role (see FIG. 7).

To confirm changes in the body of short-chain fatty acids known as anti-inflammatory agents, which provide a renal protective effect and an improvement effect of the intestinal environment, feces were collected on the last day of administration of BP121 to analyze the amount of short-chain fatty acids. As a result, acetic acid, propionic acid, and butyric acid were all confirmed to be significantly increased, and the total short-chain fatty acids were confirmed to be 4.1 times higher than the cisplatin-induced group (see FIG. 8).

Test Example 7: Evaluation of Short-Chain Fatty Acid Production Ability Over Time To confirm whether the change in the amount of short-chain fatty acids discharged to feces upon administration of *Lactobacillus salivarius* BP121 strain in Test Example 6 is an effect of BP121, the amount of short-chain fatty acids over time was measured through a single culture of the *Lactobacillus acidophilus* BP105 strain and the *Lactobacillus salivarius* BP121 strain. After pre-incubation for 24 hours in MRS broth, respectively, each of BP105 and BP121 was inoculated at 1% in MRS broth and incubated for 48 hours to measure culture supernatant at 0, 6, 12, 24, and 48 hours.

As a result, it was confirmed that the amount of each short-chain fatty acid was increased over time, and it was confirmed that the short-chain fatty acids were not measured in the control group that was not inoculated with bacteria (see FIG. 9).

The invention claimed is:

1. A method for inhibiting and preventing the progression of a renal disease in an animal, comprising administering a composition comprising one or more selected from the groups consisting of isolated *Lactobacillus salivarius* BP121 strain (Accession No. KCCM12170P), a culture thereof, a concentrate thereof, a paste thereof, a spray-dried material thereof, a lyophilisate thereof, a vacuum-dried material thereof, a drum-dried material thereof, a liquid thereof, and a dilution thereof, and a homogenate thereof in an effective amount to the animal, wherein the composition does not comprise a prebiotic inulin.

2. A method of claim 1, wherein the method comprises further administering one or more selected from the groups consisting of isolated *Lactobacillus acidophilus* BP105 strain (Accession No. KCCM12169P), a culture thereof, a concentrate thereof, a paste thereof, a spray-dried material thereof, a lyophilisate thereof, a vacuum-dried material thereof, a drum-dried material thereof, a liquid thereof, a dilution thereof, and a homogenate thereof.

3. A method of claim 1, wherein the *Lactobacillus salivarius* BP121 strain (Accession No. KCCM12170P) is isolated from feces of an infant.

4. A method of claim 1, wherein the *Lactobacillus salivarius* BP121 strain (Accession No. KCCM12170P) has indoxyl sulfate removal ability, p-cresol removal ability, and phosphorus absorption ability.

5. A method of claim 1, wherein the composition is a pharmaceutical composition, a dietary supplement, or a foodstuff.

6. A method of claim 1, wherein the composition is a dietary supplement or a foodstuff.

* * * * *